| United States Patent [19] | [11] | Patent Number: | 4,982,016 |
|---|---|---|---|
| Choi | [45] | Date of Patent: | Jan. 1, 1991 |

[54] CONVERSION OF DIETHYL PHENYLMALONATE TO 2-PHENYL-1,3-PROPANEDIOL

[75] Inventor: Young M. Choi, Plainsboro, N.J.

[73] Assignee: Carter-Wallace, Inc., New York, N.Y.

[21] Appl. No.: 361,888

[22] Filed: Jun. 6, 1989

[51] Int. Cl.$^5$ ............................................. C07C 29/132
[52] U.S. Cl. ...................................... 568/814; 568/811
[58] Field of Search ................ 568/811, 830, 814, 864

[56] References Cited

U.S. PATENT DOCUMENTS 2,848,459  8/1958  Pribyl et al. ........................ 558/281
4,868,345  9/1989  Drent ................................... 568/814

OTHER PUBLICATIONS

Miller et al., "Journal Organic Chem.", vol. 24, pp. 627–630, May 1959.
Brown et al., "Journal American Chemical Soc.", vol. 88(7), pp., Apr. 1966.

*Primary Examiner*—Werren B. Lone
*Attorney, Agent, or Firm*—Kevin B. Clarke

[57] ABSTRACT

Synthesis of 2-phenyl-1,3-propanediol by the selective reduction of diethyl phenylmalonate with metal hydrides in solution with heterocyclic ethers are disclosed.

2 Claims, No Drawings

CONVERSION OF DIETHYL PHENYLMALONATE TO 2-PHENYL-1,3-PROPANEDIOL

This invention relates to new and useful improvements in the preparation of organic diol compounds. More particularly, this invention relates to novel syntheses of the compound 2-phenyl-1,3-propanediol having the structure.

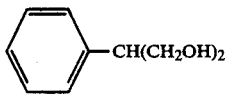

BACKGROUND

The organic diols are useful as intermediates in the preparation of diol dicarbamate compounds which are widely used in the dye industry and for medicinal purposes. U.S. Pat. Nos. 2,837,560 and 2,848,459 disclose the use of alkane and aryl diols as intermediates in the preparation of alkanediol dicarbamates and aryldiol dicarbamates respectively.

U.S. Pat. No. 2,848,459 discloses the preparation of arylpropanediols wherein an ester of an aryl acetic acid, such an benzoylacetic acid, prepared by condensing benzoic acid ester with an ester of acetic acid, employing a basic substance, such as sodium ethoxide, as a catalyst is treated with a chlorinating agent, such as sulfuryl chloride, to yield benzoyldichloroacetic acid, ethyl ester.

Benzoyldichloroacetic acid, ethyl ester is subsequently reduced to 2,2-dichloro-1-phenyl-1,3-propanediol by reduction with lithium aluminum hydride in anhydrous ether.

Similarly, U.S. Pat. No. 2,884,444 discloses the preparation of 2-phenyl-1,3-propanediol by reduction of the corresponding 2-substituted malonic ester, diethyl phenyl malonate, with lithium aluminum hydride in ethyl ether. 2-phenyl-1,3-propanediol is an intermediate in the synthesis of 2-phenyl-1,3-propanediol dicarbamate an important anticonvulsant known generically as Felbamate.

The preparation of 2-phenyl-1,3-propanediol following the prior art methods i.e., by reduction of diethyl phenyl malonate with lithium aluminum hydride in ethyl ether as taught in U.S. Pat. No. 2,884,444 gives yields ranging from a low of about 30% of product to a high of only about 50% of 2-phenyl-1,3-propanediol.

THE INVENTION

It has now been found that selective reductions of various organic esters with metal hydrides or metal hydride complexes in solution with the heterocyclic ether tetrahydrofuran has the following advantages over the aforesaid prior art methods:

1. Increased rate of reduction to give yields of from about 68% to about 98% substantially higher than the 30-50% yields achieved by the aforesaid prior art methods;
2. greater safety in carrying out the reaction; and
3. a simple and convenient isolation of 2-phenyl-1,3-propanediol from the reaction medium.

Essentially the reaction of the present invention is a reduction of diethyl phenylmalonate to 2-phenyl-1,3-propanediol which proceeds as follows:

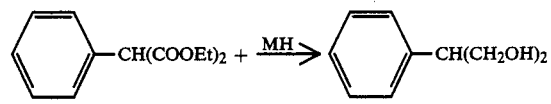

wherein diethyl phenylmalonate is added to a solution of hydride in metal hydride or complex formed with sufficient tetrahydrofuran to dissolve the hydride.

The reaction is carried out in an inert atmosphere. The metal hydride or complex is dissolved in tetrahydrofuran. The solution is cooled and an appropriate organic ester is added slowly followed by addition of a small amount of a heat transfer material. The solution is heated and maintained at elevated temperatures until completion of the reaction. The reaction mixture is cooled and an extract solvent added followed by the addition of water to quench the residual hydride. Hydrolysis is completed by the addition of hydrochloric acid. The solution is extracted with a solvent. The aqueous phase is made alkaline and further extracted with a solvent. The resulting organic phases are then combined, washed, dried and concentrated to yield the crude diol which is the recrystallized from a solvent mixture.

The procedure of the present invention has the following advantages over prior art methods:

(a) The stoichiometric amount of hydride (3H/ester and alpha hydrogen) is sufficient for the reduction to the alcohol stage.
(b) A steady increase in the concentration of reactants caused by solvent distillation results in an increase in the rate of reduction.
(c) Higher temperatures also increase the rate of reduction.
(d) The added heat transfer materials and keep the contents of the reaction vessel in a fluid state preventing the "bumping" of the contents.
(e) The isolation procedure as detailed below is simple and convenient.
   (i) To the reaction mixture is added extract solvent and the mixture then quenched with water to destroy any residual hydride.
   (ii) The addition of a strong acid in amounts equal to the amount of hydride used at 0° C. lead to a homogeneous solution.
   (iii) The aqueous layer, saturated with an alkalizing agent, is extracted with ether. The extract is dried and the solvent removed under vacuum.
   (iv) The crude diol is recrystallized from a mixture of hexane/toluene/ether (10:5:1).

The following examples are representative but not limitive of the chemical compounds prepared in accordance with the invention.

EXAMPLE 1

REDUCTION OF DIETHYL PHENYLMALONIC ACID ESTER TO 2-PHENYL-1,3-PROPANEDIOL

The reaction is carried out in a nitrogen atmosphere in a predried 250 ml RB flask with a side arm and a distillation apparatus leading to a nitrogen outlet. 180 mmoles of lithium aluminum hydride is added to the flask in sufficient tetrahydrofuran to dissolve the lithium aluminum hydride. The solution is cooled with rapid stirring to about 0° C. and 30 mmoles of diethyl phenylmalonic acid ester is slowly added followed by four ml of dry xylene which functions as a heat transfer material and prevents the contents of the flask from "bumping". The solution is heated to about 135° C. and maintained at such temperature for approximately two hours. The reaction mixture is cooled to about 0° C. and an extract solvent composed of equal parts tetrahydrofuran and ethyl ether is added and residual hydride is quenched with water. 90 ml of 2N hydrochloric acid is added to complete hydrolysis. The solution is then extracted twice with ether, the aqueous phase is made alkaline (pH 9-10) with a saturated potassium carbonate solution and extracted with ether. The organic phases are combined, washed with saturated potassium carbonate solution, dried over anhydrous magnesium sulfate and concentrated under reduced pressure to yield crude 2-phenyl-1,3-propanediol. Purified 2-phenyl-1,3-propanediol (mp 51°-53° C.) was obtained by recrystallization from a mixture of hexane/toluene/ether (10:5:1) in a yield of 72%.

EXAMPLE 2

Example 1 was repeated except that lithium aluminum hydride was replaced as the reducing agent by 180 mmoles of lithium borohydride and the reaction time was about four hours. Purified 2-phenyl-1,3-propanediol (mp 51°-53° C.) was obtained in a yield of 72%.

EXAMPLE 3

Example 1 was repeated except that aluminum hydride replaced lithium aluminum hydride as the reducing agent. Purified 2-phenyl-1,3-propanediol was obtained in a yield of 71%.

The compound prepared in accordance with the processes of the present invention is a useful intermediate in the preparation of the drug 2-phenyl-1,3-propanediol dicarbamate, felbamate, which has utility as an anticonvulsant suitable for use in tablet, pill, capsule and injectable forms.

The following examples describe the preparation of felbamate, 2-phenyl-1,3-propanediol dicarbamate, employing the 2-phenyl-1,3-propanediol prepared in accordance with the present invention as an intermediate.

EXAMPLE 4

2-phenyl-1,3-propanediol dicarbamate by urethane exchange method:

20 g of 2-phenyl-1,3-propanediol and 25 g of ethyl urethane were dissolved in 320 ml of anhydrous toluene. 3 g of aluminum isopropylate were added and the mixture distilled to remove ethanol formed in the condensation of ethyl urethane with 2-phenyl-1,3-propanediol. The ethanol distills in the form of an azeotrope with toluene. Distillation is continued until essentially the theoretical quantity of ethanol has been removed. The toluene is distilled from the mixture under reduced pressure, and the resulting solid is extracted with hot aqueous isopropanol solution. From this solution, upon cooling, is obtained 16.5 g of purified 2-phenyl-1,3-propanediol dicarbamate representing a yield of approximately 52% of theoretical. The purified product is soluble to only a slight extent in water at room temperature and has a melting point of 151°-152° C.

Analysis-Calculated for $C_{11}H_{14}N_2O_4$:N,11.8. Found: N,11.7,

Alternatively, 2-phenyl-1,3-propanediol can be converted to 2-phenyl-1,3-propanediol dicarbamate by reacting 2-phenyl-1,3-propanediol with phosgene to form the corresponding dichlorocarbonate derivatives. This reaction is promoted by the addition to the reacting compounds of acid combining agents such as sodium hydroxide, antipyrine, dialkylaniline and the like. The dichlorocarbonate derivative is then converted to the dicarbamate by ammoniation, using either anhydrous or aqueous ammonia.

The use of phosgene to convert diols to dicarbamates is well known, however, it has been found in copending U.S. patent application Ser. No. 07/057,457 filed June 3, 1987 that the acid combining agents of the prior art method may be replaced by ethers, e.g. ethyl ether or tetrahydrofuran thereby allowing the reaction to be run in solution with no precipitates to be separated and no necessity to recover and purify the acid combining agents. Moreover substantially improved yields of 2-phenyl-1,3-propanediol dicarbamate are obtained when this modified phosgene process is used.

Example 5 more fully sets forth the improved synthesis of 2-phenyl-1,3-propanediol dicarbamate according to said method.

EXAMPLE 5

2-PHENYL 1,3-PROPANEDIOL DICARBAMATE BY MODIFIED PHOSGENE METHOD 30.4 g (0.2 mole) of 2-phenyl-1,3-propanediol is dissolved in 100 ml of toluene and 35 g of tetrahydrofuran at room temperature. 30 ml of phosgene (0.44 moles) is passed into the solution while maintaining the temperature below 25° C. The solution is stirred for about 1 hour at room temperature after the phosgene addition. The tetrahydrofuran solution is dripped into 140 ml of concentrated NH$_4$OH held at 0° C. Additional water, i.e., 100 ml may be added to improve the stirring. Stirring is continued for 1½ hours at room temperature and concentrated in vacuo on a steam bath to remove most of the tetrahydrofuran. 150 ml of water is added and the mixture stirred 1 hour at room temperature. The mixture is filtered, the filtrate washed with water and dried in vacuo at 50° C. Yield 46 g M.P. 149°-151° C. of crude 2-phenyl-1,3-propanediol dicarbamate (96.6%). Recrystallization from 450 ml of methanol yields 36 g of 2-phenyl-1,3-propanediol dicarbamate (75.6%).

It should be understood that the above examples are illustrative of the best mode of the invention herein. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A method for the preparation of 2-phenyl-1,3-propanedial in high yields which comprises dissolving a member selected from the group consisting of aluminum hydride, Lithium aluminum hydride and Lithium borohydride in Tetrahydrofuran, cooling the solution and slowly adding diethyl phenylmalonate and dry xylene, heating and maintaining the solution at elevated temperatures of about 135° C. until completion of the reaction, cooling the reaction mixture and recovering the desired 2-phenyl-1,3-propanediol.

2. A method as claimed in claim 1 wherein said preparation is carried out under inert atmosphere.

* * * * *